(12) United States Patent
Nita et al.

(10) Patent No.: US 10,682,151 B2
(45) Date of Patent: Jun. 16, 2020

(54) ULTRASOUND CATHETER DEVICES AND METHODS

(71) Applicant: FlowCardia, Inc., Tempe, AZ (US)

(72) Inventors: Henry Nita, Redwood City, CA (US); Jeff Sarge, Fremont, CA (US); Richard Spano, Gilroy, CA (US)

(73) Assignee: Flowcardia, Inc., Franklin Lakes, NJ (US)

( * ) Notice: Subject to any disclaimer, the term of this patent is extended or adjusted under 35 U.S.C. 154(b) by 178 days.

(21) Appl. No.: 15/997,056

(22) Filed: Jun. 4, 2018

(65) Prior Publication Data

US 2018/0280044 A1    Oct. 4, 2018

Related U.S. Application Data

(63) Continuation of application No. 14/090,926, filed on Nov. 26, 2013, now Pat. No. 10,004,520, which is a
(Continued)

(51) Int. Cl.
 *A61B 17/22* (2006.01)
 *A61B 17/225* (2006.01)
 *A61B 17/00* (2006.01)

(52) U.S. Cl.
 CPC .... *A61B 17/22004* (2013.01); *A61B 17/2251* (2013.01); *A61B 17/22012* (2013.01);
 (Continued)

(58) Field of Classification Search
 CPC .......... A61B 17/22004; A61B 17/2251; A61B 2017/00477; A61B 2017/22014
 See application file for complete search history.

(56) References Cited

U.S. PATENT DOCUMENTS

| | | |
|---|---|---|
| 3,296,620 A | 1/1967 | Rodda |
| 3,433,226 A | 3/1969 | Boyd |
| | (Continued) | |

FOREIGN PATENT DOCUMENTS

| | | |
|---|---|---|
| AU | 2007240154 A1 | 1/2008 |
| DE | 2256127 A1 | 5/1974 |
| | (Continued) | |

OTHER PUBLICATIONS

Japanese Office Action for Japanese Application No. 2010-134566, dated Mar. 2, 2012.
(Continued)

*Primary Examiner* — Lauren P Farrar

(57) ABSTRACT

A method of operating an ultrasound catheter includes providing an elongate catheter body having at least a first lumen; providing a housing coupled with a proximal end of the elongate catheter body, the housing having an inner cavity; providing a fluid inlet in fluid communication with at least one of the first lumen and the inner cavity; providing a sonic connector coupled to a proximal portion of an ultrasound transmission member; providing vibration absorption O-rings disposed in the inner cavity around at least a portion of the ultrasound transmission member, the plurality of vibration absorption O-rings being located distal to the sonic connector; and delivering fluid to the fluid inlet to supply the fluid at least distally into the first lumen of the elongate catheter body to dissipate heat received from the ultrasound transmission member in the first lumen of the elongate catheter body.

10 Claims, 5 Drawing Sheets

Related U.S. Application Data continuation of application No. 13/019,263, filed on Feb. 1, 2011, now Pat. No. 8,617,096, which is a continuation of application No. 12/428,183, filed on Apr. 22, 2009, now Pat. No. 8,790,291, which is a continuation of application No. 10/927,966, filed on Aug. 26, 2004, now Pat. No. 7,540,852.

(52) U.S. Cl.
CPC ............ *A61B 2017/00477* (2013.01); *A61B 2017/22014* (2013.01)

(56) References Cited

U.S. PATENT DOCUMENTS

| | | |
|---|---|---|
| 3,565,062 A | 2/1971 | Kurls |
| 3,585,082 A | 6/1971 | Siller |
| 3,612,038 A | 10/1971 | Halligan |
| 3,631,848 A | 1/1972 | Muller |
| 3,679,378 A | 7/1972 | Impe et al. |
| 3,719,737 A | 3/1973 | Vaillancourt et al. |
| 3,739,460 A | 6/1973 | Addis et al. |
| 3,823,717 A | 7/1974 | Pohlman et al. |
| 3,835,690 A | 9/1974 | Leonhardt et al. |
| 3,839,841 A | 10/1974 | Amplatz |
| 3,896,811 A | 7/1975 | Storz |
| 4,016,882 A | 4/1977 | Broadwin et al. |
| 4,033,331 A | 7/1977 | Guss et al. |
| 4,136,700 A | 1/1979 | Broadwin et al. |
| 4,337,090 A | 6/1982 | Harrison |
| 4,368,410 A | 1/1983 | Hance et al. |
| 4,417,578 A | 11/1983 | Banko |
| 4,425,115 A | 1/1984 | Wuchinich |
| 4,486,680 A | 12/1984 | Bonnet et al. |
| 4,505,767 A | 3/1985 | Quin |
| 4,545,767 A | 10/1985 | Suzuki et al. |
| 4,565,589 A | 1/1986 | Harrison |
| 4,565,787 A | 1/1986 | Bossle et al. |
| 4,572,184 A | 2/1986 | Stohl et al. |
| 4,664,112 A | 5/1987 | Kensey et al. |
| 4,665,906 A | 5/1987 | Jervis |
| 4,679,558 A | 7/1987 | Kensey et al. |
| 4,700,705 A | 10/1987 | Kensey et al. |
| 4,721,117 A | 1/1988 | Mar et al. |
| 4,750,902 A | 6/1988 | Wuchinich et al. |
| 4,808,153 A | 2/1989 | Parisi |
| 4,811,743 A | 3/1989 | Stevens |
| 4,827,911 A | 5/1989 | Broadwin et al. |
| 4,838,853 A | 6/1989 | Parisi |
| 4,854,325 A | 8/1989 | Stevens |
| 4,870,953 A | 10/1989 | DonMicheal et al. |
| 4,886,060 A | 12/1989 | Wiksell |
| 4,920,954 A | 5/1990 | Alliger et al. |
| 4,923,462 A | 5/1990 | Stevens |
| 4,924,863 A | 5/1990 | Sterzer |
| 4,931,047 A | 6/1990 | Broadwin et al. |
| 4,936,281 A | 6/1990 | Stasz |
| 4,936,845 A | 6/1990 | Stevens |
| 5,000,185 A | 3/1991 | Yock |
| 5,015,227 A | 5/1991 | Broadwin et al. |
| 5,026,384 A | 6/1991 | Farr et al. |
| 5,030,357 A | 7/1991 | Lowe |
| 5,046,503 A | 9/1991 | Schneiderman |
| 5,053,008 A | 10/1991 | Bajaj |
| 5,058,570 A | 10/1991 | Idemoto et al. |
| 5,076,276 A | 12/1991 | Sakurai et al. |
| 5,091,205 A | 2/1992 | Fan |
| 5,100,423 A | 3/1992 | Fearnot |
| 5,109,859 A | 5/1992 | Jenkins |
| 5,114,414 A | 5/1992 | Buchbinder |
| 5,116,350 A | 5/1992 | Stevens |
| 5,127,917 A | 7/1992 | Niederhauser et al. |
| 5,156,143 A | 10/1992 | Booquet et al. |
| 5,163,421 A | 11/1992 | Bernstein et al. |
| 5,171,216 A | 12/1992 | Dasse et al. |
| 5,180,363 A | 1/1993 | Idemoto et al. |
| 5,183,470 A | 2/1993 | Wettermann |
| 5,195,955 A | 3/1993 | Don Michael |
| 5,215,614 A | 6/1993 | Wijkamp et al. |
| 5,217,565 A | 6/1993 | Kou et al. |
| 5,221,255 A | 6/1993 | Mahurkar et al. |
| 5,226,421 A | 7/1993 | Frisbie et al. |
| 5,234,416 A | 8/1993 | Macaulay et al. |
| 5,238,004 A | 8/1993 | Sahatjian et al. |
| 5,242,385 A | 9/1993 | Strukel |
| 5,243,997 A | 9/1993 | Uflacker et al. |
| 5,248,296 A | 9/1993 | Alliger |
| 5,255,669 A | 10/1993 | Kubota et al. |
| 5,267,954 A | 12/1993 | Nita |
| 5,269,291 A | 12/1993 | Carter |
| 5,269,297 A | 12/1993 | Weng et al. |
| 5,269,793 A | 12/1993 | Simpson |
| 5,287,858 A | 2/1994 | Hammerslag et al. |
| 5,290,229 A | 3/1994 | Paskar |
| 5,304,115 A | 4/1994 | Pflueger, Russell et al. |
| 5,304,131 A | 4/1994 | Paskar |
| 5,312,328 A | 5/1994 | Nita et al. |
| 5,318,014 A | 6/1994 | Carter |
| 5,318,570 A | 6/1994 | Hood et al. |
| 5,324,255 A | 6/1994 | Passafaro et al. |
| 5,324,260 A | 6/1994 | O'Neill et al. |
| 5,325,860 A | 7/1994 | Seward et al. |
| 5,326,342 A | 7/1994 | Pflueger et al. |
| 5,328,004 A | 7/1994 | Fannin et al. |
| 5,329,927 A | 7/1994 | Gardineer et al. |
| 5,341,818 A | 8/1994 | Abrams et al. |
| 5,342,292 A | 8/1994 | Nita et al. |
| 5,344,395 A | 9/1994 | Whalen et al. |
| 5,346,502 A | 9/1994 | Estabrook et al. |
| 5,362,309 A | 11/1994 | Carter |
| 5,368,557 A | 11/1994 | Nita |
| 5,368,558 A | 11/1994 | Nita et al. |
| 5,376,084 A | 12/1994 | Bacich et al. |
| 5,378,234 A | 1/1995 | Hammerslag et al. |
| 5,380,274 A | 1/1995 | Nita |
| 5,380,316 A | 1/1995 | Aita et al. |
| 5,382,228 A | 1/1995 | Nita et al. |
| 5,383,460 A | 1/1995 | Jang et al. |
| 5,389,096 A | 2/1995 | Aita et al. |
| 5,391,144 A | 2/1995 | Sakurai et al. |
| 5,397,293 A | 3/1995 | Alliger et al. |
| 5,397,301 A | 3/1995 | Pflueger et al. |
| 5,405,318 A | 4/1995 | Nita |
| 5,409,483 A | 4/1995 | Campbell et al. |
| 5,417,672 A | 5/1995 | Nita et al. |
| 5,417,703 A | 5/1995 | Brown et al. |
| 5,421,923 A | 6/1995 | Clarke et al. |
| 5,427,118 A | 6/1995 | Nita et al. |
| 5,431,168 A | 7/1995 | Webster, Jr. |
| 5,431,663 A | 7/1995 | Carter |
| 5,443,078 A | 8/1995 | Uflacker |
| 5,447,509 A | 9/1995 | Mills et al. |
| 5,449,369 A | 9/1995 | Imran |
| 5,451,209 A | 9/1995 | Ainsworth et al. |
| 5,465,733 A | 11/1995 | Hinohara et al. |
| 5,474,531 A | 12/1995 | Carter |
| 5,480,379 A | 1/1996 | La Rosa |
| 5,484,398 A | 1/1996 | Stoddard |
| 5,487,757 A | 1/1996 | Truckai et al. |
| 5,507,738 A | 4/1996 | Ciervo |
| 5,516,043 A | 5/1996 | Manna et al. |
| 5,527,273 A | 6/1996 | Manna et al. |
| 5,540,656 A | 7/1996 | Pflueger et al. |
| 5,542,917 A | 8/1996 | Nita et al. |
| 5,597,497 A | 1/1997 | Dean et al. |
| 5,597,882 A | 1/1997 | Schiller et al. |
| 5,607,421 A | 3/1997 | Jeevanandam et al. |
| 5,611,807 A | 3/1997 | O'Boyle |
| 5,618,266 A | 4/1997 | Liprie |
| 5,626,593 A | 5/1997 | Imran |
| 5,627,365 A | 5/1997 | Chiba et al. |
| 5,649,935 A | 7/1997 | Kremer et al. |
| 5,658,282 A | 8/1997 | Daw et al. |
| 5,685,841 A | 11/1997 | Mackool |

(56) References Cited

U.S. PATENT DOCUMENTS

| | | |
|---|---|---|
| 5,695,460 A | 12/1997 | Siegel et al. |
| 5,695,507 A | 12/1997 | Auth et al. |
| 5,715,825 A | 2/1998 | Crowley |
| 5,720,724 A | 2/1998 | Ressemann et al. |
| 5,728,062 A | 3/1998 | Brisken |
| 5,738,100 A | 4/1998 | Yagami et al. |
| 5,797,876 A | 8/1998 | Spears et al. |
| 5,816,923 A | 10/1998 | Milo et al. |
| 5,827,203 A | 10/1998 | Nita |
| 5,827,971 A | 10/1998 | Hale et al. |
| 5,830,222 A | 11/1998 | Makower |
| 5,846,218 A | 12/1998 | Brisken et al. |
| 5,893,838 A | 4/1999 | Daoud et al. |
| 5,895,397 A | 4/1999 | Jang et al. |
| 5,902,287 A | 5/1999 | Martin |
| 5,904,667 A | 5/1999 | Falwell |
| 5,916,192 A | 6/1999 | Nita et al. |
| 5,916,912 A | 6/1999 | Ames et al. |
| 5,935,142 A | 8/1999 | Hood |
| 5,935,144 A | 8/1999 | Estabrook |
| 5,937,301 A | 8/1999 | Gardner et al. |
| 5,944,737 A | 8/1999 | Tsonton et al. |
| 5,957,882 A | 9/1999 | Nita et al. |
| 5,957,899 A | 9/1999 | Spears et al. |
| 5,964,223 A | 10/1999 | Baran |
| 5,967,984 A | 10/1999 | Chu et al. |
| 5,971,949 A | 10/1999 | Levin et al. |
| 5,976,119 A | 11/1999 | Spears et al. |
| 5,989,208 A | 11/1999 | Nita |
| 5,989,275 A | 11/1999 | Estabrook et al. |
| 5,997,497 A | 12/1999 | Nita et al. |
| 6,004,280 A | 12/1999 | Buck et al. |
| 6,007,499 A | 12/1999 | Martin et al. |
| 6,007,514 A | 12/1999 | Nita |
| 6,022,309 A | 2/2000 | Celliers et al. |
| 6,024,764 A | 2/2000 | Schroeppel |
| 6,029,671 A | 2/2000 | Stevens et al. |
| 6,030,357 A | 2/2000 | Daoud et al. |
| 6,051,010 A | 4/2000 | DiMatteo et al. |
| 6,113,558 A | 9/2000 | Rosenschein et al. |
| 6,123,698 A | 9/2000 | Spears et al. |
| 6,142,971 A | 11/2000 | Daoud et al. |
| 6,149,596 A | 11/2000 | Bancroft |
| 6,159,176 A | 12/2000 | Broadwin et al. |
| 6,165,127 A | 12/2000 | Crowley |
| 6,165,188 A | 12/2000 | Saadat et al. |
| 6,179,809 B1 | 1/2001 | Khairkhahan et al. |
| 6,180,059 B1 | 1/2001 | Divino, Jr. et al. |
| 6,190,353 B1 | 2/2001 | Makower et al. |
| 6,206,842 B1 | 3/2001 | Tu et al. |
| 6,210,356 B1 | 4/2001 | Anderson et al. |
| 6,217,543 B1 | 4/2001 | Anis et al. |
| 6,217,565 B1 | 4/2001 | Cohen |
| 6,217,588 B1 | 4/2001 | Jerger et al. |
| 6,221,015 B1 | 4/2001 | Yock |
| 6,231,546 B1 | 5/2001 | Milo et al. |
| 6,231,587 B1 | 5/2001 | Makower |
| 6,235,007 B1 | 5/2001 | Divino, Jr. et al. |
| 6,241,692 B1 | 6/2001 | Tu et al. |
| 6,241,703 B1 | 6/2001 | Levin et al. |
| 6,248,087 B1 | 6/2001 | Spears et al. |
| 6,277,084 B1 | 8/2001 | Abele et al. |
| 6,283,983 B1 | 9/2001 | Makower et al. |
| 6,287,271 B1 | 9/2001 | Dubrul et al. |
| 6,287,285 B1 | 9/2001 | Michal et al. |
| 6,287,317 B1 | 9/2001 | Makower et al. |
| 6,296,620 B1 | 10/2001 | Gesswein et al. |
| 6,302,875 B1 | 10/2001 | Makower et al. |
| 6,309,358 B1 | 10/2001 | Okubo |
| 6,315,741 B1 | 11/2001 | Martin et al. |
| 6,315,754 B1 | 11/2001 | Daoud et al. |
| 6,331,171 B1 | 12/2001 | Cohen |
| 6,346,192 B2 | 2/2002 | Buhr et al. |
| 6,379,378 B1 | 4/2002 | Werneth |
| 6,387,109 B1 | 5/2002 | Davison et al. |
| 6,387,324 B1 | 5/2002 | Patterson et al. |
| 6,394,956 B1 | 5/2002 | Chandrasekaran et al. |
| 6,398,736 B1 | 6/2002 | Seward |
| 6,409,673 B2 | 6/2002 | Yock |
| 6,416,533 B1 | 7/2002 | Gobin et al. |
| 6,423,026 B1 | 7/2002 | Gesswein et al. |
| 6,427,118 B1 | 7/2002 | Suzuki |
| 6,433,464 B2 | 8/2002 | Jones |
| 6,434,418 B1 | 8/2002 | Neal et al. |
| 6,450,975 B1 | 9/2002 | Brennan et al. |
| 6,454,757 B1 | 9/2002 | Nita et al. |
| 6,454,997 B1 | 9/2002 | Divino, Jr. et al. |
| 6,484,052 B1 | 11/2002 | Visuri et al. |
| 6,491,707 B2 | 12/2002 | Makower et al. |
| 6,494,891 B1 | 12/2002 | Cornish et al. |
| 6,494,894 B2 | 12/2002 | Mirarchi |
| 6,500,141 B1 | 12/2002 | Irion et al. |
| 6,508,781 B1 | 1/2003 | Brennan et al. |
| 6,508,784 B1 | 1/2003 | Shu |
| 6,511,458 B2 | 1/2003 | Milo et al. |
| 6,524,251 B2 | 2/2003 | Rabiner et al. |
| 6,533,766 B1 | 3/2003 | Patterson et al. |
| 6,544,215 B1 | 4/2003 | Bencini et al. |
| 6,547,754 B1 | 4/2003 | Evans et al. |
| 6,551,337 B1 | 4/2003 | Rabiner et al. |
| 6,554,846 B2 | 4/2003 | Hamilton et al. |
| 6,555,059 B1 | 4/2003 | Myrick et al. |
| 6,558,502 B2 | 5/2003 | Divino, Jr. et al. |
| 6,562,031 B2 | 5/2003 | Chandrasekaran et al. |
| 6,573,470 B1 | 6/2003 | Brown et al. |
| 6,576,807 B1 | 6/2003 | Brunelot et al. |
| 6,582,387 B2 | 6/2003 | Derek et al. |
| 6,589,253 B1 | 7/2003 | Cornish et al. |
| 6,595,989 B1 | 7/2003 | Schaer |
| 6,596,235 B2 | 7/2003 | Divino, Jr. et al. |
| 6,602,467 B1 | 8/2003 | Divino, Jr. et al. |
| 6,602,468 B2 | 8/2003 | Patterson et al. |
| 6,605,217 B2 | 8/2003 | Buhr et al. |
| 6,607,698 B1 | 8/2003 | Spears et al. |
| 6,613,280 B2 | 9/2003 | Myrick et al. |
| 6,615,062 B2 | 9/2003 | Ryan et al. |
| 6,616,617 B1 | 9/2003 | Ferrera et al. |
| 6,622,542 B2 | 9/2003 | Derek et al. |
| 6,623,448 B2 | 9/2003 | Slater |
| 6,635,017 B1 | 10/2003 | Moehring et al. |
| 6,650,923 B1 | 11/2003 | Lesh et al. |
| 6,652,547 B2 | 11/2003 | Rabiner et al. |
| 6,660,013 B2 | 12/2003 | Rabiner et al. |
| 6,676,900 B1 | 1/2004 | Divino, Jr. et al. |
| 6,682,502 B2 | 1/2004 | Bond et al. |
| 6,685,657 B2 | 2/2004 | Jones |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,810 B2 | 2/2004 | Peacock, III et al. |
| 6,702,748 B1 | 3/2004 | Nita et al. |
| 6,702,750 B2 | 3/2004 | Yock |
| 6,719,715 B2 | 4/2004 | Newman et al. |
| 6,719,725 B2 | 4/2004 | Milo et al. |
| 6,729,334 B1 | 5/2004 | Baran |
| 6,733,451 B2 | 5/2004 | Rabiner et al. |
| 6,758,846 B2 | 7/2004 | Goble et al. |
| 6,761,698 B2 | 7/2004 | Shibata et al. |
| 6,855,123 B2 | 2/2005 | Nita |
| 6,866,670 B2 | 3/2005 | Rabiner et al. |
| 6,936,025 B1 | 8/2005 | Evans et al. |
| 6,936,056 B2 | 8/2005 | Nash et al. |
| 6,942,620 B2 | 9/2005 | Nita et al. |
| 6,942,677 B2 | 9/2005 | Nita et al. |
| 6,955,680 B2 | 10/2005 | Satou et al. |
| 7,004,173 B2 | 2/2006 | Sparks et al. |
| 7,004,176 B2 | 2/2006 | Lau |
| 7,056,294 B2 | 6/2006 | Khairkhahan et al. |
| 7,131,983 B2 | 11/2006 | Murakami |
| 7,137,963 B2 | 11/2006 | Nita et al. |
| 7,150,853 B2 | 12/2006 | Lee et al. |
| 7,166,098 B1 | 1/2007 | Steward et al. |
| 7,220,233 B2 | 5/2007 | Nita et al. |
| 7,267,650 B2 | 9/2007 | Chow et al. |

(56) References Cited

U.S. PATENT DOCUMENTS

| | | |
|---|---|---|
| 7,297,131 B2 | 11/2007 | Nita |
| 7,335,180 B2 | 2/2008 | Nita et al. |
| 7,341,569 B2 | 3/2008 | Soltani et al. |
| 7,384,407 B2 | 6/2008 | Rodriguez et al. |
| 7,393,338 B2 | 7/2008 | Nita |
| 7,421,900 B2 | 9/2008 | Karasawa et al. |
| 7,425,198 B2 | 9/2008 | Moehring et al. |
| 7,494,468 B2 | 2/2009 | Rabiner et al. |
| 7,503,895 B2 | 3/2009 | Rabiner et al. |
| 7,540,852 B2 | 6/2009 | Nita et al. |
| 7,604,608 B2 | 10/2009 | Nita et al. |
| 7,621,902 B2 | 11/2009 | Nita et al. |
| 7,621,929 B2 | 11/2009 | Nita et al. |
| 7,648,478 B2 | 1/2010 | Soltani et al. |
| 7,771,358 B2 | 8/2010 | Moehring et al. |
| 7,775,994 B2 | 8/2010 | Lockhart |
| 7,776,025 B2 | 8/2010 | Bobo, Jr. |
| 7,819,013 B2 | 10/2010 | Chan et al. |
| 7,850,623 B2 | 12/2010 | Griffin et al. |
| 7,935,108 B2 | 5/2011 | Baxter et al. |
| 7,938,819 B2 | 5/2011 | Kugler et al. |
| 7,955,293 B2 | 6/2011 | Nita et al. |
| 8,043,251 B2 | 10/2011 | Nita et al. |
| 8,083,727 B2 | 12/2011 | Kugler et al. |
| 8,133,236 B2 | 3/2012 | Nita |
| 8,221,343 B2 | 7/2012 | Nita et al. |
| 8,226,566 B2 | 7/2012 | Nita |
| 8,246,643 B2 | 8/2012 | Nita |
| 8,308,677 B2 | 11/2012 | Nita et al. |
| 8,506,519 B2 | 8/2013 | Nita |
| 8,617,096 B2 | 12/2013 | Nita et al. |
| 8,632,560 B2 | 1/2014 | Pal et al. |
| 8,647,296 B2 | 2/2014 | Moberg et al. |
| 8,690,819 B2 | 4/2014 | Nita et al. |
| 8,790,291 B2 | 7/2014 | Nita et al. |
| 8,974,446 B2 | 3/2015 | Nguyen et al. |
| 9,107,590 B2 | 8/2015 | Hansmann et al. |
| 9,265,520 B2 | 2/2016 | Nita |
| 9,282,984 B2 | 3/2016 | Nita |
| 9,314,258 B2 | 4/2016 | Nita et al. |
| 9,770,250 B2 | 9/2017 | Nita et al. |
| 2003/0009153 A1 | 1/2003 | Brisken et al. |
| 2003/0036705 A1 | 2/2003 | Hare et al. |
| 2003/0199817 A1 | 10/2003 | Thompson et al. |
| 2003/0216732 A1 | 11/2003 | Truckai et al. |
| 2003/0225332 A1 | 12/2003 | Okada et al. |
| 2004/0024393 A1 | 2/2004 | Nita et al. |
| 2005/0033311 A1 | 2/2005 | Guldfeldt et al. |
| 2005/0228286 A1 | 10/2005 | Messerly et al. |
| 2006/0206039 A1 | 9/2006 | Wilson et al. |
| 2006/0264809 A1 | 11/2006 | Hansmann et al. |
| 2008/0071343 A1 | 3/2008 | Mayberry et al. |
| 2008/0208084 A1 | 8/2008 | Horzewski et al. |
| 2008/0221506 A1 | 9/2008 | Rodriguez et al. |
| 2010/0023037 A1 | 1/2010 | Nita et al. |
| 2011/0105960 A1 | 5/2011 | Wallace |
| 2011/0130834 A1 | 6/2011 | Wilson et al. |
| 2011/0237982 A1 | 9/2011 | Wallace |
| 2011/0313328 A1 | 12/2011 | Nita |
| 2012/0130475 A1 | 5/2012 | Shaw |
| 2012/0311844 A1 | 12/2012 | Nita et al. |
| 2012/0330196 A1 | 12/2012 | Nita |
| 2014/0243712 A1 | 8/2014 | Humayun et al. |
| 2015/0150571 A1 | 6/2015 | Nita et al. |
| 2015/0190660 A1 | 7/2015 | Sarge et al. |
| 2015/0359651 A1 | 12/2015 | Wübbeling |
| 2016/0128717 A1 | 5/2016 | Nita |
| 2016/0183956 A1 | 6/2016 | Nita |
| 2016/0271362 A1 | 9/2016 | Van Liere |
| 2017/0354428 A1 | 12/2017 | Nita et al. |

FOREIGN PATENT DOCUMENTS

| | | |
|---|---|---|
| DE | 2438648 A1 | 2/1976 |
| DE | 8910040 U1 | 12/1989 |
| DE | 3821836 A1 | 1/1990 |
| DE | 4042435 C2 | 2/1994 |
| EP | 0005719 A1 | 12/1979 |
| EP | 0316789 A2 | 5/1989 |
| EP | 0316796 A2 | 5/1989 |
| EP | 0376562 A2 | 7/1990 |
| EP | 0379156 A2 | 7/1990 |
| EP | 00394583 A2 | 10/1990 |
| EP | 0443256 A1 | 8/1991 |
| EP | 0541249 A2 | 5/1993 |
| EP | 0820728 A2 | 1/1998 |
| EP | 1323481 A2 | 7/2003 |
| GB | 1106957 | 3/1968 |
| JP | 61-272045 A | 12/1986 |
| JP | H2-7150 U | 10/1988 |
| JP | 01-099547 | 4/1989 |
| JP | 3-67608 U | 7/1991 |
| JP | 6086822 A | 3/1994 |
| JP | H07500752 A | 1/1995 |
| JP | 7116260 A | 5/1995 |
| JP | 9-503137 | 3/1997 |
| JP | 10-216140 | 8/1998 |
| JP | 2000-291543 | 10/2000 |
| JP | 2001-104356 | 4/2001 |
| JP | 2001-321388 | 11/2001 |
| JP | 2002-186627 | 7/2002 |
| JP | 2005-253874 | 9/2005 |
| JP | 2006-522644 A | 10/2006 |
| JP | 2007520255 A | 7/2007 |
| WO | 8705739 A1 | 9/1987 |
| WO | 8705793 A1 | 10/1987 |
| WO | 8906515 A1 | 7/1989 |
| WO | 9001300 A1 | 2/1990 |
| WO | 9004362 A1 | 5/1990 |
| WO | 9107917 A2 | 6/1991 |
| WO | 9211815 A2 | 7/1992 |
| WO | 9308750 A2 | 5/1993 |
| WO | 9316646 A1 | 9/1993 |
| WO | 9412140 A1 | 6/1994 |
| WO | 9414382 A1 | 7/1994 |
| WO | 9508954 A1 | 4/1995 |
| WO | 9509571 A1 | 4/1995 |
| WO | 9515192 A1 | 6/1995 |
| WO | 9635469 A1 | 11/1996 |
| WO | 9705739 A1 | 2/1997 |
| WO | 9721462 A1 | 6/1997 |
| WO | 9745078 A1 | 12/1997 |
| WO | 9827874 A1 | 7/1998 |
| WO | 9835721 A2 | 8/1998 |
| WO | 9851224 A2 | 11/1998 |
| WO | 9852637 A1 | 11/1998 |
| WO | 9925412 A2 | 5/1999 |
| WO | 0053341 A1 | 9/2000 |
| WO | 0067830 A1 | 11/2000 |
| WO | 03039381 A1 | 5/2003 |
| WO | 2004012609 A1 | 2/2004 |
| WO | 2004093736 A2 | 11/2004 |
| WO | 2004112888 A2 | 12/2004 |
| WO | 2005053769 A2 | 6/2005 |
| WO | 2006049593 A1 | 5/2006 |
| WO | 2014022716 A2 | 2/2014 |

OTHER PUBLICATIONS

Sehgal, et al., Ultrasound-Assisted Thrombolysis, Investigative Radiology, 1993, vol. 28, Issue 10, pp. 939-943.

Siegel, et al., "In Vivo Ultrasound Arterial Recanalization of Atherosclerotic Total Occlusions", Journal of the American College of Cardiology, Feb. 1990, vol. 15, No. 2, pp. 345-351.

"What is Electron Beam Curing?" downloaded from web on Nov. 14, 2002, 4 pages total. <http://www.ms.oml.gov/researchgroups/composites/new%20orccmt%20pages/pages/ebwha>.

Calhoun et al., "Electron-Beam Systems for Medical Device Sterilization", downloaded from web on Oct. 8, 2002 <http://www.devicelink.com/mpb/archive/97/07/002.html> 7 pages total.

Definition of the term "coupled", retrieved on May 18, 2013. <http://www.merriam-webster.com/dictionary/couple> 1 page total.

(56) References Cited

OTHER PUBLICATIONS

"E-Beam Theory" RDI-IBA Technology Group, downloaded from web on Oct. 8, 2002 <http://www.ebeamrdi/EbeamTheory.htm> 2 pages total.

Noone, D.: Experimental and Numerical Investigation of Wire Waveguides for Therapeutic Ultrasound Angioplasty. M.Eng. Dublin City University. 2008.

Definition of the term "connected", retrieved on Sep. 21, 2013. <www.thefreedictionary.com/connected> 1 page total.

Supplemental European Search Report dated Nov. 5, 2009 for European Application No. EP03766931.

International Search Report dated Oct. 28, 2003 for PCT Application No. PCT/US2003/023468.

Extended European Search Report dated Mar. 22, 2012 for European Application No. EP11188799.

International Search Report dated Dec. 23, 2005 for PCT Application No. PCT/US2004/019378.

Extended European Search Report for Patent Application No. 06718204.8, dated May 30, 2012.

International Search Report dated Aug. 1, 2013 for PCT Application No. PCT/US2013/053306.

International Preliminary Report dated Aug. 1, 2013 for PCT Application No. PCT/US2013/053306.

Written Opinion dated Aug. 1, 2013 for PCT Application No. PCT/US2013/053306.

Extended European Search Report dated Mar. 5, 2012 for European Application No. 12153606.4-1269.

Margaret Fyfe et al., Mast cell degranulation and increased vascular permeability induced by 'therapeutic' ultrasound in the rate ankle joint, Br. J. exp. Path., 1984, vol. 65, pp. 671-676.

"Irradiation, Biological, and Other Technologies: E-beam, Biological, and Sharps Treatment Systems", Non-Incineration Medical Waste Treatment Technologies, Aug. 2001, Chapter 9, pp. 69-74, Health Care Without Harm, Washington, DC.

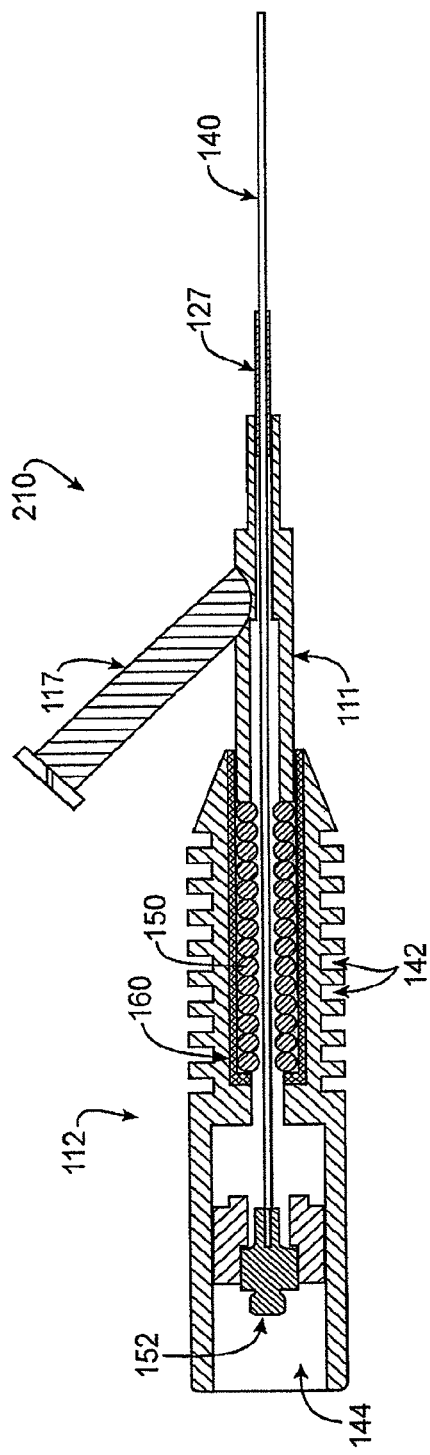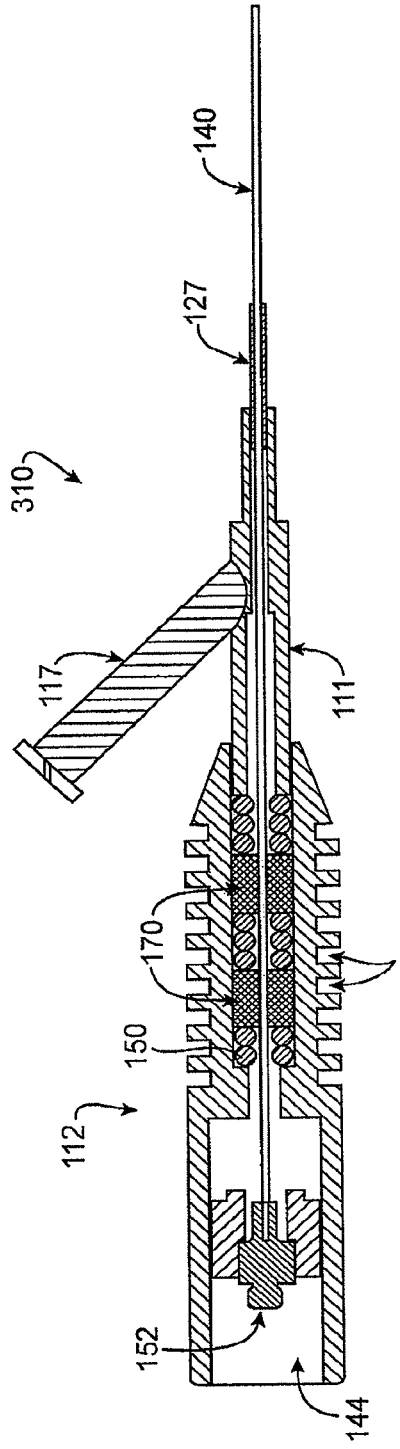

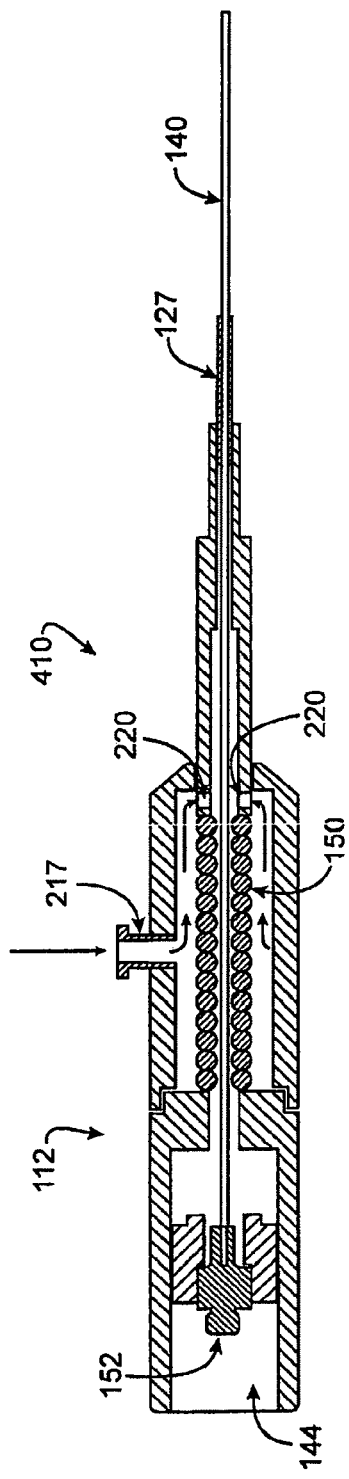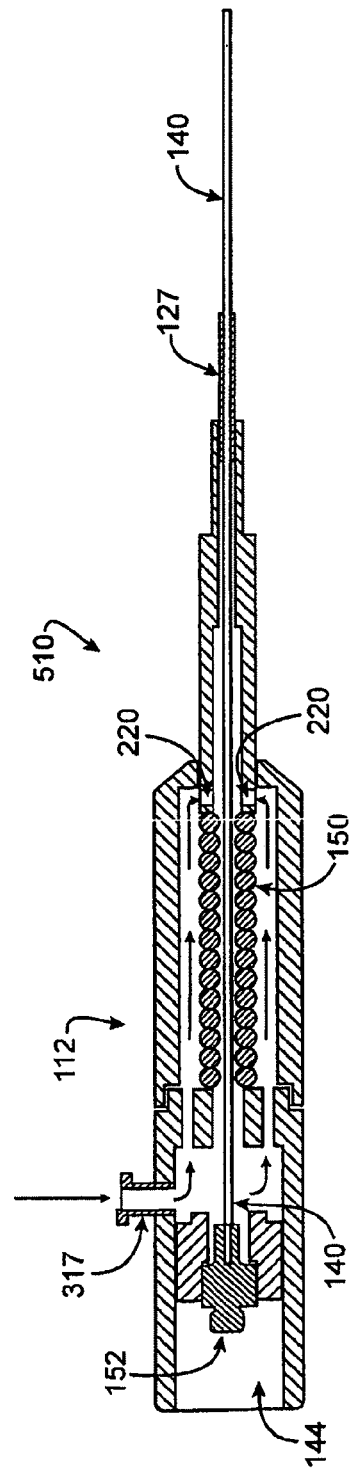

ULTRASOUND CATHETER DEVICES AND METHODS

CROSS-REFERENCE TO RELATED APPLICATIONS

This application is a continuation of application Ser. No. 14/090,926, filed on Nov. 26, 2013, now issued as U.S. Pat. No. 10,004,520 on Jun. 26, 2018, which is a continuation of application Ser. No. 13/019,263, filed on Feb. 1, 2011, now issued as U.S. Pat. No. 8,617,096 on Dec. 31, 2013, which is a continuation of application Ser. No. 12/428,183, filed on Apr. 22, 2009, now issued as U.S. Pat. No. 8,790,291 on Jul. 29, 2014, which is a continuation of application Ser. No. 10/927,966, filed Aug. 26, 2004, now issued as U.S. Pat. No. 7,540,852 on Jun. 2, 2009, all of which are hereby expressly incorporated by reference in their entireties.

BACKGROUND OF THE INVENTION

The present invention relates generally to medical devices and methods. More specifically, the present invention relates to ultrasound catheter devices and methods for treating occlusive intravascular lesions.

Catheters employing various types of ultrasound transmitting members have been successfully used to ablate or otherwise disrupt obstructions in blood vessels. Specifically, ablation of atherosclerotic plaque or thromboembolic obstructions from peripheral blood vessels such as the femoral arteries has been particularly successful. Various ultrasonic catheter devices have been developed for use in ablating or otherwise removing obstructive material from blood vessels. For example, U.S. Pat. Nos. 5,267,954 and 5,380,274, issued to an inventor of the present invention and hereby incorporated by reference, describe ultrasound catheter devices for removing occlusions. Other examples of ultrasonic ablation devices for removing obstructions from blood vessels include those described in U.S. Pat. No. 3,433,226 (Boyd), U.S. Pat. No. 3,823,717 (Pohlman, et al.), U.S. Pat. No. 4,808,153 (Parisi), U.S. Pat. No. 4,936,281 (Stasz), U.S. Pat. No. 3,565,062 (Kuris), U.S. Pat. No. 4,924,863 (Sterzer), U.S. Pat. No. 4,870,953 (Don Michael, et al), and U.S. Pat. No. 4,920,954 (Alliger, et al.), as well as other patent publications WO87-05739 (Cooper), WO89-06515 (Bernstein, et al.), WO90-0130 (Sonic Needle Corp.), EP316789 (Don Michael, et al.), DE3,821,836 (Schubert) and DE2438648 (Pohlman). While many ultrasound catheters have been developed, however, improvements are still being pursued.

Typically, an ultrasonic catheter system for ablating occlusive material includes three basic components: an ultrasound generator, an ultrasound transducer, and an ultrasound catheter. The generator converts line power into a high frequency current that is delivered to the transducer. The transducer contains piezoelectric crystals which, when excited by the high frequency current, expand and contract at high frequency. These small, high-frequency expansions (relative to an axis of the transducer and the catheter) are amplified by the transducer horn into vibrational energy. The vibrations are then transmitted from the transducer through the ultrasound catheter via an ultrasound transmission member (or wire) running longitudinally through the catheter. The transmission member transmits the vibrational energy to the distal end of the catheter where the energy is used to ablate or otherwise disrupt a vascular obstruction.

To effectively reach various sites for treatment of intravascular occlusions, ultrasound catheters of the type described above typically have lengths of about 150 cm or longer. To permit the advancement of such ultrasound catheters through small and/or tortuous blood vessels such as the aortic arch, coronary vessels, and peripheral vasculature of the lower extremities, the catheters (and their respective ultrasound transmission wires) must typically be sufficiently small and flexible. Also, due to attenuation of ultrasound energy along the long, thin, ultrasound transmission wire, a sufficient amount of vibrational energy must be applied at the proximal end of the wire to provide a desired amount of energy at the distal end.

One continuing challenge in developing ultrasound catheters for treating vascular occlusions is to provide adequate vibrational energy at the distal end of a catheter device without overheating the ultrasound transmission wire. Generally, increasing the amount of power input to the ultrasound transmission wire causes the temperature of the wire to increase. Overheating may occur anywhere along the length of the transmission wire, from its proximal connection with the ultrasound transducer to the distal tip of the wire. Overheating of the wire, along with the mechanical stresses placed on the wire from propagating ultrasound waves, can cause wire breakage, thus shortening the useful life of the catheter device. Furthermore, it is generally desirable to ablate an occlusion via the ultrasound vibrations and not by heating the occlusion, since heating causes a denaturalization process that reduces the efficacy of the ultrasound ablation.

Some ultrasound catheters use irrigation fluid to attempt to control the temperature of the ultrasound transmission wire, but such irrigation cooling techniques are not always effective. Other devices use swapped frequencies to change frequency nodes and anti-nodes, thus moving a heat source from point to point along the transmission wire. However, a given ultrasound transmission wire resonates at the fundamental frequency for which it is designed, and thus changing frequencies essentially requires turning the ultrasound device on and off, which reduces the efficacy of the device. Some ultrasound catheter devices include one or more absorption members at the proximal end for absorbing unwanted vibrations of the ultrasound transmission wire. Such absorbers, however, do not address the heat generation issue and, in fact, may cause increased heating from frictional forces.

Therefore, a need exists for improved ultrasound catheter devices and methods that provide ablation or disruption of vascular occlusions. Ideally, such ultrasound catheters would provide a desired level of power at a distal end of the device while also preventing overheating of the device's ultrasound transmission member. Ideally, such devices would address ultrasound transmission wire overheating at its proximal connection with a catheter device as well as along the length of the wire. At least some of these objectives will be met by the present invention.

SUMMARY OF THE INVENTION

In one aspect of the invention, an ultrasound catheter for disrupting occlusions in blood vessels includes: an elongate flexible catheter body having a proximal end, a distal end and at least one lumen; an ultrasound transmission member extending longitudinally through the lumen of the catheter body and having a proximal end and a distal end; a distal head coupled with the distal end of the ultrasound transmission member and disposed adjacent the distal end of the catheter body; a sonic connector coupled with the proximal end of the ultrasound transmission member for coupling the ultrasound transmission member with an ultrasound transducer device; and a proximal housing coupled with the proximal end of the catheter body and housing the sonic connector and a proximal portion of the ultrasound transmission wire. The proximal housing includes at least one heat dissipation feature for dissipating heat from the proximal portion of the ultrasound transmission member.

In some embodiments, the heat dissipation feature comprises one or more portions of the housing constructed of a heat conductive material. For example, the heat conductive material may include, but is not limited to, metal, polymer, glass, rubber, combinations thereof, or the like. Additionally (or alternatively), the heat dissipation feature may comprise multiple surface features on the housing to increase a surface area of the housing. Such surface features may include, for example, grooves, notches, waves, dips and/or the like. In some embodiments, an additional or alternative heat dissipation feature comprises at least one conductive material disposed within the housing, at least partially encircling the ultrasound transmission member, to conduct heat away from the ultrasound transmission member. In one embodiment, the conductive material may be disposed adjacent one or more vibration absorption members surrounding the ultrasound transmission member. Optionally, multiple separate conductive members may be disposed between multiple vibration absorption members to at least partially encircle the ultrasound transmission member. In another embodiment, the conductive material is arranged over one or more vibration absorption members surrounding the ultrasound transmission member.

In some embodiments, the heat dissipation feature comprises at least one fluid inlet for allowing passage of one or more heat dissipating fluids into an inner cavity of the housing. In some embodiments, the inner cavity of the housing is in fluid communication with the lumen of the catheter body, such that fluid introduced into the inner cavity passes through and out a distal end of the catheter body lumen. In some embodiments, the inlet is disposed along the housing such that the heat dissipating fluid(s) passing through the inlet contact at least one vibration absorption member disposed over the ultrasound transmission member. The inlet may also be disposed along the housing such that the heat dissipating fluid(s) passing through the inlet contact the sonic connector and a portion of the ultrasound transmission member. Some devices further include a refrigeration device coupled with the catheter for refrigerating a fluid to be introduced through the fluid inlet. Optionally, the device may further include a guidewire tube extending through at least a portion of the catheter body for allowing passage of a guidewire. In one embodiment, a sidewall of the guidewire tube includes a plurality of apertures for allowing fluid introduced into the lumen of the catheter body to pass into and through the guidewire tube.

In some embodiments, at least a portion of the proximal housing comprises a material adapted to change color when the temperature of the housing changes. In one embodiment, for example, the material comprises a thermochromic pigment. The thermochromic pigment, in one embodiment, may change from a first color to a second color when the temperature of the housing reaches approximately 45° Celsius and changes from the second color to the first color when the temperature of the housing drops below approximately 45° Celsius.

In another aspect of the present invention, an ultrasound catheter for disrupting occlusions in blood vessels includes: an elongate flexible catheter body having a proximal end, a distal end and at least one lumen; an ultrasound transmission member extending longitudinally through the lumen of the catheter body and having a proximal end and a distal end; a distal head coupled with the distal end of the ultrasound transmission member and disposed adjacent the distal end of the catheter body; a sonic connector coupled with the proximal end of the ultrasound transmission member for coupling the ultrasound transmission member with an ultrasound transducer device; a proximal housing coupled with the proximal end of the catheter body and housing the sonic connector and a proximal portion of the ultrasound transmission wire; and heat dissipation means for dissipating heat from the ultrasound transmission member. According to various embodiments, heat dissipation means may include any suitable members, devices, attachments or the likes, such as but not limited to those described above. Any features described above may be applied to this ultrasound catheter.

In another aspect of the present invention, an ultrasound catheter system for disrupting occlusions in blood vessels includes an ultrasound catheter device, an ultrasound generator removably coupled with the ultrasound catheter device, and a fluid cooling device removably coupled with the ultrasound catheter device for cooling one or more heat dissipating fluids to be passed through the catheter device. The ultrasound catheter device itself includes: an elongate flexible catheter body having a proximal end, a distal end and at least one lumen; an ultrasound transmission member extending longitudinally through the lumen of the catheter body and having a proximal end and a distal end; a distal head coupled with the distal end of the ultrasound transmission member and disposed adjacent the distal end of the catheter body; a sonic connector coupled with the proximal end of the ultrasound transmission member for coupling the ultrasound transmission member with an ultrasound transducer device; and a proximal housing coupled with the proximal end of the catheter body and housing the sonic connector and a proximal portion of the ultrasound transmission wire. The housing includes at least one fluid inlet for allowing passage of one or more heat dissipating fluids into an inner cavity of the housing. Again, the ultrasound catheter may include any of the features described above.

In another aspect of the present invention, a method for disrupting an occlusion in a blood vessel involves positioning an ultrasound catheter in the blood vessel such that a distal end of the catheter is adjacent the occlusion; transmitting ultrasound energy to an ultrasound transmission member of the ultrasound catheter to disrupt the occlusion into multiple occlusion fragments, and passing a cooled irrigation fluid through the ultrasound catheter to dissipate heat away from the ultrasound transmission member. In some embodiments, for example, the cooled fluid has a temperature between about 1° C. and about 22° C. Any suitable cooled fluid may be used, such as but not limited to saline, thrombolytic agents, antiplatelet drugs, lysing agents, anticoagulants and/or the like. In some embodiments, the method further involves cooling the irrigation fluid to a desired temperature, using a refrigeration device coupled with the ultrasound catheter. In one embodiment, cooled fluid is passed continuously through the ultrasound catheter during an occlusion disruption procedure. Alternatively, the cooled fluid may be passed through the ultrasound catheter while the catheter is activated, with fluid passage being automatically stopped when the ultrasound catheter is deactivated.

In another aspect of the present invention, a method for disrupting an occlusion in a blood vessel involves positioning an ultrasound catheter in the blood vessel such that a distal end of the catheter is adjacent the occlusion, transmitting ultrasound energy to an ultrasound transmission member of the ultrasound catheter to disrupt the occlusion into multiple occlusion fragments, and passing an oxygen supersaturated irrigation fluid through the ultrasound catheter to dissipate heat away from the ultrasound transmission member. In some embodiments, for example, the oxygen supersaturated irrigation fluid comprises oxygen supersaturated saline solution. In other embodiments, the oxygen supersaturated irrigation fluid comprises saline solution combined with a radiopaque contrast material. The oxygen supersaturated fluid may be kept at any suitable temperature. In some embodiments, the fluid is kept at room temperature, while in other embodiments it is kept at between about 1° C. and about 22° C.

In another aspect of the present invention, a method for disrupting an occlusion in a blood vessel involves positioning an ultrasound catheter in the blood vessel such that a distal end of the catheter is adjacent the occlusion, transmitting ultrasound energy to an ultrasound transmission member of the ultrasound catheter to disrupt the occlusion into multiple occlusion fragments, and passing a lubricious irrigation fluid through the ultrasound catheter to dissipate heat away from the ultrasound transmission member and reduce friction between the ultrasound transmission member and an ultrasound catheter body. For example, in some embodiments, the lubricious irrigation fluid comprises an emulsion. In one embodiment, the emulsion comprises olive oil, egg yolk, phospholipids, glycerin, sodium deoxycholate, L-histidine, disodium CDTA, sodium hydroxide and water. In some embodiments, the emulsion has a pH of between about 8.0 and about 9.0. The lubricious fluid may be kept at any suitable temperature. In some embodiments, the fluid is kept at room temperature, while in other embodiments it is kept at between about 1° C. and about 22° C.

These and other aspects and embodiments of the present invention are described in further detail below, in reference to the attached drawing figures.

BRIEF DESCRIPTION OF THE DRAWINGS

FIG. 4 is cross-sectional side view of a proximal portion of an ultrasound catheter device having heat dissipation means according to another embodiment of the present invention;

FIG. 5 is cross-sectional side view of a proximal portion of an ultrasound catheter device having heat dissipation means according to another embodiment of the present invention;

FIG. 6 is cross-sectional side view of a proximal portion of an ultrasound catheter device, with a proximal housing of the device having a fluid inlet aperture according to an embodiment of the present invention;

FIG. 7 is cross-sectional side view of a proximal portion of an ultrasound catheter device, with a proximal housing of the device having a fluid inlet aperture according to another embodiment of the present invention.

DETAILED DESCRIPTION OF CERTAIN EMBODIMENTS

Ultrasound catheter devices and methods of the present invention provide for disruption of occlusions in blood vessels. Catheter devices generally include a catheter body, an ultrasound energy transmission member disposed within the catheter body and a distal head coupled with the energy transmission member and disposed at or near the distal end of the catheter body. The ultrasound transmission member transmits ultrasound energy from an ultrasound transducer to the distal head, causing the head to vibrate and, thus, disrupt vascular occlusions. A number of improved features of such ultrasound catheter devices are described more fully below.

Figure 1:
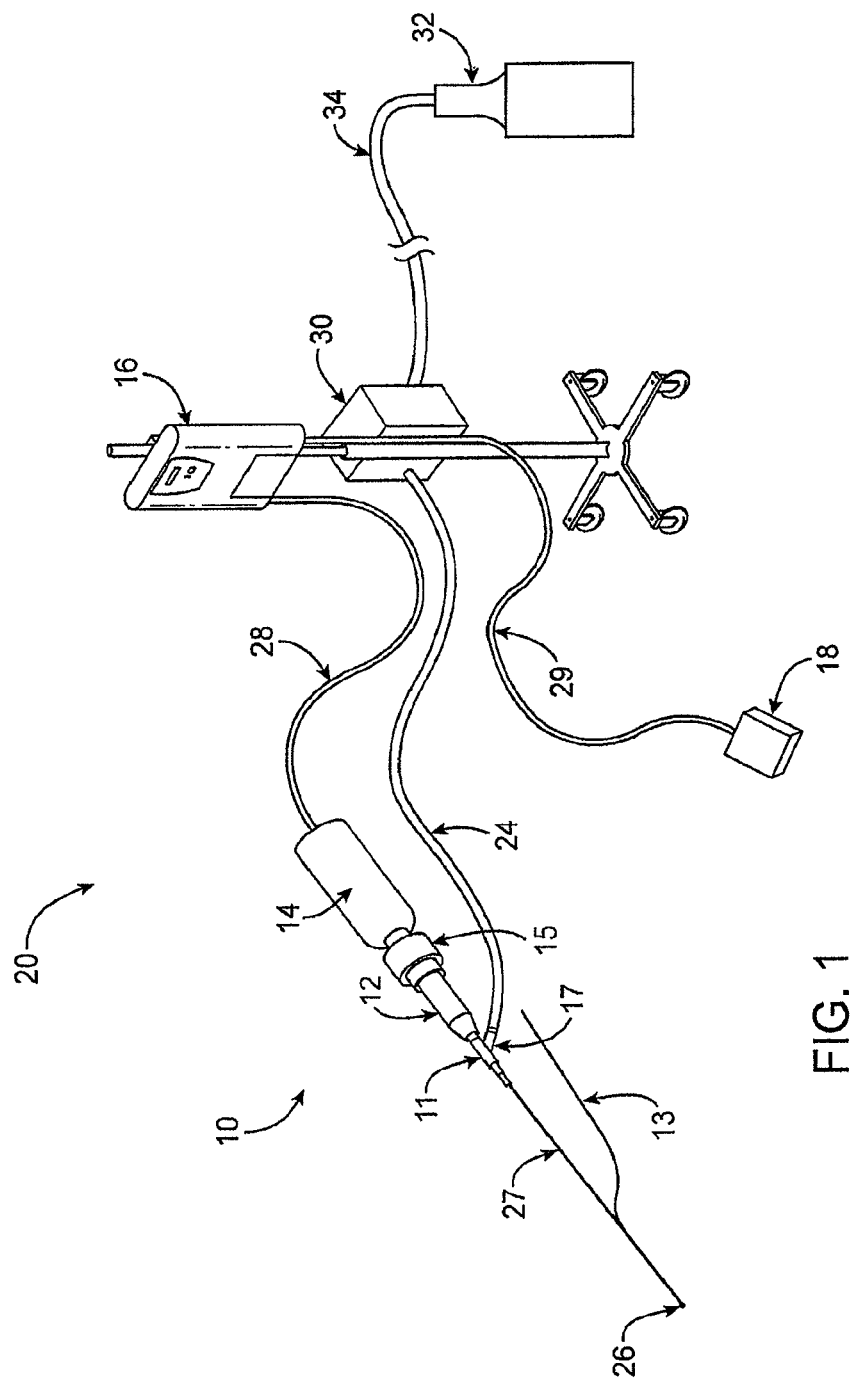
FIG. 1 is a perspective view of an ultrasound catheter system according to an embodiment of the present invention.

Referring now to FIG. 1, one embodiment of an ultrasound catheter system 20 suitably includes an ultrasound catheter device 10 and an ultrasound generator 16. Catheter device 10 suitably includes a distal head 26 for disrupting occlusions, a catheter body 27, and a proximal end connector 12 for coupling catheter device 10 with an ultrasound transducer 14. Ultrasound transducer 14 is coupled with ultrasound generator 16 via a connector 28, and generator is coupled with a foot-actuated on/off switch 18 via another connector 29. Generator 16 provides ultrasonic energy to transducer 14 and, thus, to ultrasound catheter 10. Catheter device 10 further includes an ultrasound transmission member (or "wire"—not shown) that extends through the catheter body 27 and transmits energy from the transducer 14 to the distal head 26. Some embodiments of device 10 include a rapid exchange guidewire 13 and guidewire port, while other embodiments include a proximal guidewire port for over the wire guidewire delivery. In some embodiments, transducer 14 further includes a securing device 15 for enhancing coupling of catheter 10 to transducer 14. The various components of system 20 may be coupled via any suitable means. Connectors 28, 29 may comprise an electric cord or cable or any other suitable connecting devices for coupling on/off switch 18, generator 16 and transducer 14. In an alternative embodiment, on/off switch 18 is located on generator 16.

In addition to proximal connector 12, ultrasound catheter device 10 may include one or more other various components, such as a Y-connector 11 including a fluid inlet port 17 (or aperture) for passage of irrigation fluid. Inlet port 17 may be removably coupled with an irrigation tube 24, which in one embodiment may be coupled with a fluid refrigeration (or "fluid cooling") device 30. Refrigeration device 30 may, in turn, be coupled with a fluid container 32 via a connector tube 34. This irrigation apparatus may be used for introducing one or more fluids into catheter device 10. Fluid may be used to cool any part of the device, such as the ultrasound transmission member, thus helping reduce wear and tear of device 10. In some embodiments, fluid inlet port 17 is located farther proximally on proximal connector 12, to allow fluid to be applied within connector 12. In some embodiments, refrigerated fluid is used, while in other embodiments irrigation fluid may be kept at room temperature. In various embodiments, oxygen supersaturated fluid, lubricious fluid, or any other suitable fluid or combination of fluids may be used, and again, such fluids may be refrigerated or kept room temperature. In an alternative embodiment to that shown in FIG. 1, refrigeration device 30 and fluid container 32 are combined in one device.

Generally, catheter device 10 may include any suitable number of side-arms or ports for passage of a guidewire, application of suction, infusing and/or withdrawing irrigation fluid, dye and/or the like, or any other suitable ports or connections. Also, ultrasound catheters 10 of the present invention may be used with any suitable proximal devices, such as any suitable ultrasound transducer 14, ultrasound generator 16, coupling device(s) and/or the like. Therefore, the exemplary embodiment shown in FIG. 1 and any following descriptions of proximal apparatus or systems for use with ultrasound catheters 10 should not be interpreted to limit the scope of the present invention as defined in the appended claims.

Figure 2:
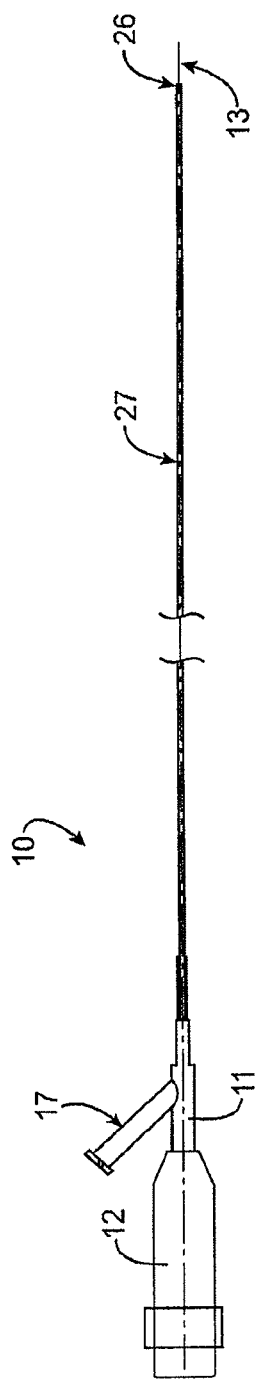
FIG. 2 is a side view of an ultrasound catheter device according to an embodiment of the present invention.

Referring now to FIG. 2, an enlarged view of catheter device 10 is shown. Proximal connector 12, Y-connector 11, inlet port 17, catheter body 27, distal head 26 and guidewire 13 are all shown. Catheter body 27 is generally a flexible, tubular, elongate member, having any suitable diameter and length for reaching a vascular occlusion for treatment. In one embodiment, for example, catheter body 27 preferably has an outer diameter of between about 0.5 mm and about 5.0 mm. In other embodiments, as in catheters intended for use in relatively small vessels, catheter body 27 may have an outer diameter of between about 0.25 mm and about 2.5 mm. Catheter body 27 may also have any suitable length. As discussed briefly above, for example, some ultrasound catheters have a length in the range of about 150 cm. However, any other suitable length may be used without departing from the scope of the present invention. Examples of catheter bodies similar to those which may be used in the present invention are described in U.S. Pat. Nos. 5,267,954 and 5,989,208, which were previously incorporated herein by reference.

Features of the present invention may be applied to any of a number of ultrasound catheter devices. For more detailed description of exemplary ultrasound catheter devices, reference may be made to U.S. patent application Ser. Nos. 10/229,371, 10/345,078, 10/375,903, 10/410,617 and 10/722,209, which were all previously incorporated by reference. In various alternative embodiments, aspects of the present invention may be applied to any other suitable catheter devices.

Figure 3:
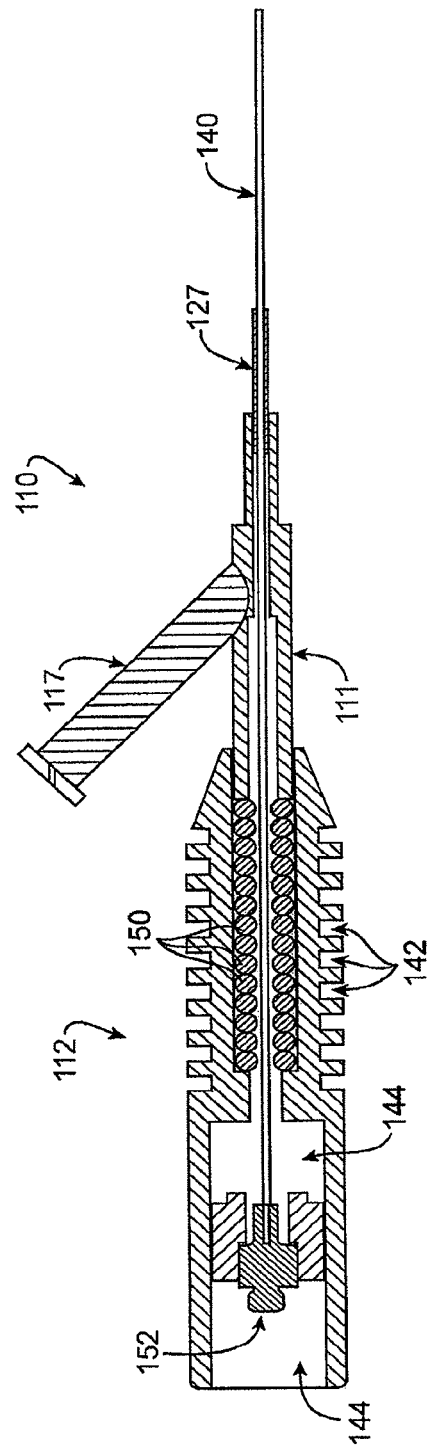
FIG. 3 is cross-sectional side view of a proximal portion of an ultrasound catheter device having heat dissipation means according to an embodiment of the present invention.

Referring now to FIG. 3, a proximal portion of one embodiment of an ultrasound catheter device 110 is shown in cross-section. An ultrasound transmission wire 140 extends from a sonic connector 152 distally to a distal end (not shown) of catheter device 110. A catheter body 127 of device 110 is shown only in part, whereas catheter body 127 typically extends distally to (or near) the distal end of device 110. Catheter device 110 also includes a proximal housing 112 (or "proximal connector"), having an inner bore 144 (or "inner cavity") in which sonic connector 152, a portion of ultrasound transmission member 140 and one or more vibration absorption members 150 reside. Housing 112 is coupled with a Y-connector 111, which includes a fluid inlet port 117 (or aperture), and Y-connector 111 is coupled with catheter body 127.

In various embodiments, housing 112 may suitably include one or more surface features 142 for increasing the overall surface area of the outer surface of housing 112. Increased surface area enhances the ability of housing 112 to dissipate heat generated by ultrasound transmission member 140 out of catheter device 110. Surface features 142 may have any suitable size or shape, such as ridges, jags, undulations, grooves or the like, and any suitable number of surface features 142 may be used. Additionally, housing 112 may be made of one or more heat dissipating materials, such as aluminum, stainless steel, any other conductive metal(s), or any suitable non-metallic conductive material(s).

In most embodiments, ultrasound transmission member 140, wire, or wave guide extends longitudinally through a lumen of catheter body 127 to transmit ultrasonic energy from an ultrasound transducer (not shown), connected to the proximal end of proximal housing 112, to the distal end of catheter device 110. Ultrasound transmission member 140 may be formed of any material capable of effectively transmitting ultrasonic energy from the ultrasound transducer to the distal end of catheter body 127, including but not limited to metals such as pure titanium or aluminum, or titanium or aluminum alloys. Again, additional details of ultrasound transmission members 140 may be found in the patent applications incorporated by reference above. Similarly, reference may be made to the incorporated patent applications for descriptions of housing 112, sonic connector 152, vibration absorption members 150, Y-connector 111 and the like. For example, housing 112 and other features are described in detail in Ser. No. 10/722,209, filed Nov. 24, 2003, entitled "Steerable Ultrasound Catheter", which was previously incorporated by reference.

Ultrasound transmission member 140 typically passes from sonic connector 152, through bore 144 and Y-connector 111, and then through catheter body 127. Fluid inlet port 117 is in fluid communication with a lumen in Y-connector, 117 which is in fluid communication with a lumen extending through catheter body 127. Thus, fluid introduced into fluid inlet port 117 is typically free to flow into and through catheter body 127 to contact ultrasound transmission member 140. Fluid may flow out of catheter body 127 through apertures in the distal head (not shown) or through any other suitable apertures or openings, such as apertures located in catheter body 127 itself. Any suitable fluid may be passed through fluid inlet port 117 and catheter body 127, such as refrigerated fluid, lubricious fluid, super-saturated saline or contrast/saline mixture, or the like. Cooling and/or lubricating ultrasound transmission member 140 may reduce friction and/or wear and tear of ultrasound transmission member 140, thus prolonging the useful life of ultrasound catheter device 110 and enhancing its performance.

Additionally, the temperature and flow rate of a coolant liquid may be specifically controlled to maintain the temperature of ultrasound transmission member 140 at a desired temperature within its optimal working range. In particular, in embodiments of the invention where ultrasound transmission member 140 is formed of a metal alloy which exhibits optimal physical properties (e.g. super elasticity) within a specific range of temperatures, the temperature and flow rate of coolant liquid infused through fluid inlet port 117 may be specifically controlled to maintain the temperature of ultrasound transmission member 140 within a range of temperatures at which it demonstrates its most desirable physical properties. For example, in embodiments of the invention where ultrasound transmission member 140 is formed of a shape memory alloy which exhibits super-elasticity when in its martensite state, but which loses super-elasticity as it transitions to an austenite state, it will be desirable to adjust the temperature and flow rate of the coolant liquid infused through fluid inlet port 117 to maintain the shape memory alloy of ultrasound transmission member 140 within a temperature range at which the alloy will remain in its martensite state and will not transition to an austenite state. The temperature at which such shape memory alloys transition from a martensite state to an austenite state is known as the "martensite transition temperature" of the material. Thus, in these embodiments, the fluid infused through port 117 will be at such temperature, and will be infused at such rate, as to maintain the shape memory alloy of ultrasound transmission member 140 below its martensite transition temperature.

As mentioned above, in one embodiment, a super-saturated fluid may be used. Use of such fluids may enhance cavitation of an occlusion, help prevent unwanted tissue damage and/or the like. Such fluids are described, for example, in U.S. Pat. Nos. 6,676,900, 6,622,542, 6,613,280, 6,607,698, 6,605,217, 6,602,468, 6,602,467, 6,596,235, 6,582,387, 6,576,807, 6,558,502, 6,555,059, 6,533,766, 6,454,997, 6,387,324, 6,346,192, 6,315,754, 6,248,087, 6,235,007, 6,180,059, 6,142,971, 6,123,698, 6,030,357, 5,976,119, 5,957,889, 5,893,838 and 5,797,876, which are hereby incorporated by reference. In another embodiment, a mixture of contrast dye and saline may be used to achieve the same or similar results.

With reference now to FIG. 4, one embodiment of an ultrasound catheter device 210 includes the features described immediately above and also includes a heat absorbing member 160 disposed within housing 112. Heat absorbing member 160 may have any suitable shape and size and may, in various embodiments, be disposed in any of a number of different locations within housing 112. Typically, heat absorbing member 160 is made of a heat absorbing material, such as but not limited to a metalized elastomer, such as a rubber material combined with a metallic powder such as aluminum powder. Of course, any other suitable heat sink or heat absorption material may be used, in alternative embodiments. In the embodiment shown, heat absorbing member 160 is generally cylindrical in shape and is disposed around vibration absorption members 150, so that it absorbs heat from ultrasound transmission member 140 and vibration absorbers 150.

Referring to FIG. 5, in an alternative embodiment an ultrasound catheter device 310 may include multiple heat absorption members 170, such as cylindrical members disposed around ultrasound transmission member 140 and in between multiple vibration absorption members 150. As is evident from FIGS. 4 and 5, any of a number of configurations of heat absorption members 160, 170 may be disposed within housing 112.

FIG. 6 demonstrates another embodiment of an ultrasound catheter device 410, which may include any of the features described above. In this embodiment, a fluid inlet port 217 is located farther proximally on housing 112 than in the earlier-described embodiments. Fluid inlet port 217 is in fluid communication with inner cavity 144 of housing 112, so that fluid (solid-tipped arrows) introduced into fluid inlet port 217 enters inner cavity 144 and contacts vibration absorption members 150 before entering the lumen of catheter body 127 via one or more proximal apertures 220. Fluid passing along and contacting vibration absorption members 150 will help dissipate heat from the members 150. As mentioned above, such fluids may be refrigerated/cooled, lubricious, oxygen supersaturated or the like. Lubricious and oxygen supersaturated fluids, in various embodiments, may be either cooled/refrigerated or at room temperature.

Referring to FIG. 7, another embodiment of an ultrasound catheter device 510 includes all the features just described, but fluid inlet port 317 is located farther proximally on housing 112. In this embodiment, fluid (solid-tipped arrows) entering fluid inlet port 317 contacts a proximal portion of ultrasound transmission member 140, proceeds distally to contact vibration absorption members 150, and then proceeds through apertures 220 into the lumen of catheter body 127. Thus, the fluid provides extra heat dissipation to the proximal portion of ultrasound transmission member 140 with which it comes in contact.

In various embodiments, the vibration absorption members 150, such as O-rings, surround a portion of ultrasound transmission members 140 for providing absorption of transverse vibration. Absorption members 150 may be used in any number or combination and have a suitable size and configuration, depending on the desired level of vibration absorption or dampening. Alternatively or additionally, other dampening structures may be used.

In various embodiments, the vibration absorption members 150 may be capable of absorbing heat. In other embodiments, the vibration absorption members 150 comprise at least one vibration absorbing material selected from the group consisting of rubbers and polymers.

Figure 8:
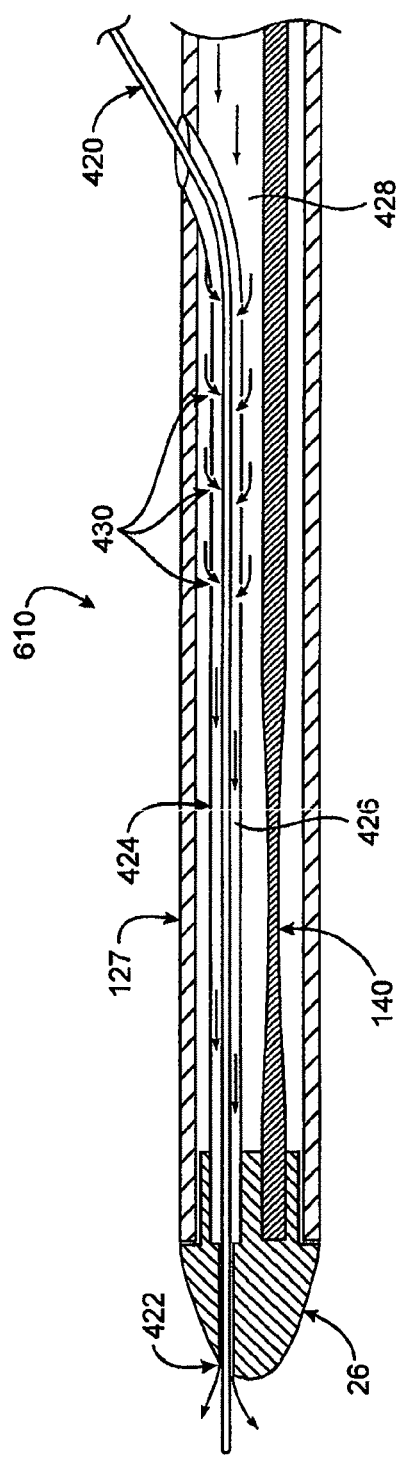
FIG. 8 is a cross-sectional side view of a distal portion of an ultrasound catheter device having a perforated guidewire tube for allowing passage of fluid therethrough according to another embodiment of the present invention

As mentioned above, in some embodiments irrigation/cooling fluid passes through a lumen of catheter body 127 and out one or more apertures in distal head 26 or elsewhere on the catheter device. In an alternative embodiment, and with reference now to FIG. 8, an ultrasound catheter device 610 may include a guidewire tube 424 that forms a guidewire lumen 426 and that includes one or more guidewire tube apertures 430 for allowing passage of fluid. Generally, a guidewire 420 may be passed through guidewire lumen 426 and out a distal aperture 422 of guidewire tube 424, located in distal head 26. Fluid (solid-tipped arrows) that is passed through a catheter body lumen 428 may flow into apertures 430 and out distal aperture 422. The fluid would thus contact ultrasound transmission member 140 during a portion of its journey through catheter body lumen 428, thus dissipating heat and/or lubricating, and would then pass out of catheter device 610 via guidewire tube 424. This configuration may be advantageous in that irrigation fluid may provide an additional lubrication inside guidewire lumen 426 to improve guidewire movement.

In one embodiment, housing 112 may include a material that changes color when its temperature increases or decreases, thus providing an indication of the temperature of the proximal portion of the catheter device. In one embodiment, for example, a thermochromic material, such as Colorcomp®. Thermochromics (provided by LNP Engineering Plastics, Inc.) may be used. Other color-change materials may be used in alternative embodiments. In various embodiments, the color of such material may change at any suitable temperatures. In one embodiment, for example, the thermochromic pigment changes from a first color to a second color when the temperature of housing 112 reaches approximately 45° Celsius and changes from the second color to the first color when the temperature of housing 112 drops below approximately 45° Celsius.

Although the invention has been described above with specific reference to various embodiments and examples, it should be understood that various additions, modifications, deletions and alterations may be made to such embodiments without departing from the spirit or scope of the invention. Accordingly, it is intended that all reasonably foreseeable additions, deletions, alterations and modifications be included within the scope of the invention as defined in the following claims.

What is claimed is:

1. A method of operating an ultrasound catheter for disrupting occlusions in blood vessels, comprising:
   providing an elongate catheter body having a proximal end, a distal end, and at least a first lumen;
   providing a housing coupled with the proximal end of the elongate catheter body, the housing having an inner cavity;

providing a fluid inlet in fluid communication with at least one of the first lumen and the inner cavity;

providing a sonic connector coupled to a proximal portion of an ultrasound transmission member, the sonic connector being completely disposed within the inner cavity and the ultrasound transmission longitudinally extending from the sonic connector through the at least one lumen of the elongate catheter body;

providing a plurality of vibration absorption O-rings disposed in the inner cavity around at least a portion of the ultrasound transmission member, the plurality of vibration absorption O-rings being located distal to the sonic connector; and delivering fluid to the fluid inlet to supply the fluid at least distally into the first lumen of the elongate catheter body to dissipate heat received from the ultrasound transmission member in the first lumen of the elongate catheter body.

2. The method of claim 1, wherein the plurality of vibration absorption O-rings is located distal to the fluid inlet.

3. The method of claim 2, comprising delivering fluid via the fluid inlet into the inner cavity in the housing, the fluid contacting a proximal portion of the ultrasound transmission member, the fluid proceeds distally to contact the plurality of vibration absorption O-rings, and the fluid proceeding distally into the first lumen of the elongate catheter body, the fluid providing heat dissipation to the ultrasound transmission member and to the plurality of vibration absorption O-rings with which the fluid comes in contact.

4. The method of claim 3, wherein each of the plurality of vibration absorption O-rings is in direct contact with an adjacent O-ring along a longitudinal length of the ultrasound transmission member and wherein each of the plurality of vibration absorption O-rings is in direct contact with the ultrasound transmission member.

5. The method of claim 4, wherein at least a first portion of the inner cavity comprises a continuous cylindrical shape, and the plurality of vibration absorption O-rings are located in the first portion of the inner cavity.

6. The method of claim 1, wherein the plurality of vibration absorption O-rings is disposed proximal to the fluid inlet.

7. The method of claim 6, wherein each of the plurality of vibration absorption O-rings is in direct contact with an adjacent O-ring along a longitudinal length of the ultrasound transmission member and wherein each of the plurality of vibration absorption O-rings is in direct contact with the ultrasound transmission member.

8. The method of claim 6, comprising controlling a temperature and a flow rate of the fluid to maintain a temperature of the ultrasound transmission member at a desired temperature.

9. The method of claim 1, wherein the housing has one or more surface features for increasing the overall surface area of an outer surface of the housing to aid in dissipating heat.

10. The method of claim 1, wherein the plurality of vibration absorption O-rings is comprised of rubber.

* * * * *